United States Patent [19]

Uchiyama et al.

[11] Patent Number: 5,122,460
[45] Date of Patent: Jun. 16, 1992

[54] METHOD OF MANUFACTURING INULOTRIOSE AND/OR INULOTETROSE USING AN EXO-TYPE HYDROLASE CAPABLE OF HYDROLYZING A FRUCTAN ONLY EVERY 3 OR 4 SUGAR UNITS FROM A TERMINAL FRUCTOSE

[75] Inventors: Takao Uchiyama, Minoo; Mishio Kawamura, Toyonaka; Reiko Sashida, Kawasaki; Makoto Ueda, Machida; Sachiko Ohba, Yokohama; Haruyuki Ohkishi, Machida, all of Japan

[73] Assignee: Mitsubishi Kasei Corporation, Tokyo, Japan

[21] Appl. No.: 734,558

[22] Filed: Jul. 23, 1991

Related U.S. Application Data

[62] Division of Ser. No. 484,243, Feb. 26, 1990.

[30] Foreign Application Priority Data

Feb. 28, 1989 [JP] Japan .................................. 1-47361
Dec. 20, 1989 [JP] Japan ................................. 1-330257

[51] Int. Cl.$^5$ .......................... C12P 19/20; C12N 1/00; C12N 1/20; C12N 1/12
[52] U.S. Cl. ...................................... 435/96; 435/886; 435/822; 435/252.35; 435/252.1
[58] Field of Search ..................... 435/96, 886, 252.35, 435/822, 252.1

[56] References Cited

U.S. PATENT DOCUMENTS 4,898,820  2/1990  Hitoshio et al. ...................... 435/95

FOREIGN PATENT DOCUMENTS 240741   10/1987  European Pat. Off. .
2219226   9/1974  France .
62-232380 10/1987  Japan .
1420528   1/1976  United Kingdom .

OTHER PUBLICATIONS

Chemical Abstracts, vol. 89, #72341x (1978).
Chemical Abstracts, vol. 95, #37854u (1981).
L. Zittan, Starch/Starke, vol. 33, (1981), Nr. 11, pp. 373-377.
Stryer, Biochemistry, 3rd Edition, pp. 337-339, W. H. Freeman and Company, New York (1988).
Ghevna et al, Catalogue of Bacterial and Phages, 17th ed., ATCC, p. 21, 1989.
Shiomi et al, "The $^{13}$C-NMR Spectra of . . . ", Agric. Biol. Chem, 54 vol. 1, pp. 215-216, 1990.
Uchiyama, "Action of Arthrobacter Urea Faciens", Biochem of Biophys. Acta., 397, pp. 153-163, 1975.
Xiao et al, "Purification and Some Properties . . . ", J. of Ferm. and Bioeng., 67, No. 4, pp. 244-248, 1989.

Primary Examiner—David M. Naff
Assistant Examiner—Michael Meller
Attorney, Agent, or Firm—Oblon, Spivak, McClelland, Maier & Neustadt

[57] ABSTRACT

The present invention is directed to a method of manufacturing inulotriose and/or inulotetrose by using an exo-type hydrolase capable of hydrolyzing a fructan only every 3 or 4 sugar units from a terminal fructose thereof, so as to produce inulotriose and/or inulotetrose, and of recovering the inulotriose and/or inulotetrose. The enzyme is produced by Streptomyces sp. MCI 2423 (FERM BP-2678) and Aureobacterium sp. MCI 2494 (FERM BP-2679).

6 Claims, No Drawings

METHOD OF MANUFACTURING INULOTRIOSE AND/OR INULOTETROSE USING AN EXO-TYPE HYDROLASE CAPABLE OF HYDROLYZING A FRUCTAN ONLY EVERY 3 OR 4 SUGAR UNITS FROM A TERMINAL FRUCTOSE

This is a division of application Ser. No. 07/484,243, filed on Feb. 26, 1990.

BACKGROUND OF THE INVENTION

1. Field of the Invention

This invention relates to a novel exo-type hydrolase (provisional name: exo-inulo-trio and tetrao-hydrase) which hydrolyzes a fructan specifically every 3–4 sugar units from the terminal fructose thereof, and to a method of manufacturing inulotriose and/or inulotetrose from a fructan using said hydrolase.

2. Prior Art

Inulotriose and inulotetrose, which respectively consist of 3 and 4 fructoses, are inulo-oligosaccharides with a high functionality (for example, bifidus factor, anticariogenicity, low calories, etc.), and they find wide application in the arts of foods and pharmaceuticals.

Conventionally, one method for preparing inulotriose and inulotetrose from a fructan has been to subject a fructan such as inulin to an acid hydrolysis reaction (JP62-232380).

According to this method, however, the main product was fructose ($F_1$) and the yield of inulo-oligosaccharides, including inulotriose and inulotetrose, was extremely poor. In addition, colored substances were produced together with a by-product such as difructose anhydride, and thus the purification of inulotriose and inulotetrose was very difficult.

Another method has also been proposed wherein a fructan is hydrolyzed by means of an enzyme to produce inulotriose and inulotetrose (Barrie E. Norman and Birgitte Hojer-pedersen, Denpun Kagaku, 36, 103 (1989)). The enzyme used for this purpose, however, was only an end-type inulinase which hydrolyzes a fructan randomly. When therefore it hydrolyzed, for example, inulin, in addition to inulotriose and inulotetrose, other inulo-oligosaccharides consisting of various different numbers of fructoses were also produced such as inulobiose ($F_2$), inulopentose ($F_5$), and inulohexose ($F_6$). Moreover, fructose itself was also produced as a by-product. Consequently the yield of inulotriose and inulotetrose was poor and the method was unsuitable for their manufacture.

We have studied on the methods by which inulotriose and inulotetrose could be manufactured from a fructan. As a result, we found a novel exo-type hydrolase (provisional name: exo-inulo-trio and tetrao-hydrase) which specifically hydrolyzes a fructan into oligosaccharides consisting of 3 to 4 fructoses.

SUMMARY OF THE INVENTION

In accordance with the present invention, there is provided a novel exo-type hydrolase which can hydrolyze a fructan every 3–4 sugar units from the terminal fructose thereof to produce inulotriose and/or inulotetrose. The present invention also provides a method of manufacturing inulotriose and/or inulotetrose, said method comprising the steps of hydrolyzing a fructan with a novel exo-type hydrolase, which can hydrolyze it every 3–4 sugar units from the terminal fructose thereof to produce inulotriose and/or inulotetrose, and of recovering said inulotriose and/or inulotetrose.

DETAILED DESCRIPTION OF THE INVENTION

A previously known enzyme(i.e., inulinase) which can produce inulo-oligosaccharides includes an endo-type hydrolase which hydrolyzes, for example, inulin randomly to produce inulo-oligosaccharides consisting of various different numbers of fructoses (Barrie E. Norman and Birgitte Hojer-Pedersen, Denpun Kagaku, 36, 103 (1989)), an exo-type hydrolase which hydrolyzes inulin to produce only fructose (Moussa Ettalibi and Jacques C. Baratti, Appl. Microbiol. Biotechnol., 36, 13 (1987)), and a hydrolase which hydrolyzes inulin to produce fructose anhydride (Takano Uchiyama et al, Biochim. Biophys. Acta, 284, 248 (1972)). The enzyme of this invention with the aforementioned property is a novel exo-type hydrolase.

The hydrolase according to the invention can be obtained from a microorganism belonging to the genus Streptomyces or Aureobacterium.

The microorganism used in this invention may be any microorganism which can produce an exo-type hydrolase with the property of hydrolyzing a fructan every 3–4 sugar units from the terminal fructose thereof to produce inulotriose and/or inulotetrose, and it is not limited to a microorganism belonging to the genus Streptomyces or Aureobacterium, their variants or their mutants.

Examples of the microorganism belonging to the genus Streptomyces or Aureobacterium are Streptomyces sp. MCI 2423 and Aureobacterium sp. MCI 2494.

These strains have been deposited under FERM BP-2679 and FERM BP-2678, respectively, in the Fermentation Reserch Institute, Agency of Industrial Science and Technology, Japan.

Of these strains we describe below the morphological characteristics, the properties on culture media, and the physiological and biochemical properties, of Streptomyces sp. MCI 2423 (hereinafter referred to as Actinomyces MCI 2423).

1. Morphological Characteristics

The culture was carried out on Bennett agar or glucose/asparagine agar medium as a sporulation medium at 27° C. for 1 week.

On Bennett's agar medium, the colonies are yellowish white at first, and change to bright olive grey depending on the formation of the aerial hyphae. Segmented, relatively short spore chains are formed on the aerial hyphae. The spore chains stand out radially in groups of about 2 to 4 spore chains, and do not form spirals. The surface of the spores is flat and smooth. The spores are shaped like short cylinders, and their dimensions are 1–1.1 $\mu$m $\times$ 1.2–1.5 $\mu$m.

On glucose/asparagine agar medium, the colonies are yellowish white. The aerial mycelium and spores are poor. Development of the vegetative mycelium is good, and the mycelium is segmented in places after about 3 to 4 days of the culture to form long spore chains.

2. Properties on Various Culture Media

| 1) Properties in various liquid media (shaking culture at 27° C. for 1 week) | |
|---|---|
| Liquid medium | Properties |

| | | |
|---|---|---|
| Bennett's medium | Develops into hyphae. No fragmentation of the hyphae is observed. | |
| Waksman's medium | Develops into hyphae. No fragmentation of the hyphae is observed. | |
| Heart infusion medium | Formation of hyphae is not observed. Hyphae are fragmented into rods. | |
| Yeast/malt extract medium | Formation of hyphae is not observed. Hyphae are fragmented. | |

2) Properties on various agar media
Properties on various agar media after culturing the strain at 27° C. for 14 days are as follows:

| Type of medium | Item* | Properties |
|---|---|---|
| Sucrose/nitrate agar medium | G | Very poor, yellowish white |
| | AM | Scant |
| | S | Abundant sporulation on the aerial and vegetative mycelium |
| | SP | Not produced |
| Glucose/asparagine agar medium | G | Good, light yellowish brown |
| | AM | Scant |
| | S | Abundant sporulation on the aerial and vegetative mycelium |
| | SP | Not produced |
| Starch/inorganic salts | G | Good, yellow-brown |
| | AM | Scant |
| | S | Abundant sporulation on aerial and vegetative mycelium |
| | SP | Not produced |
| Tyrosine agar medium (ISP 7) | G | Good, yellow-brown - greyish yellow-brown |
| | AM | Scant |
| | S | Abundant sporulation on the aerial and vegetative mycelium |
| | SP | Not produced |
| Yeast extract/ malt extract agar medium (ISP 2) | G | Good, yellow-brown - greyish yellow-brown |
| | AM | Scant |
| | S | Abundant sporulation on the aerial and vegetative mycelium |
| | SP | Not produced |
| Oatmeal agar medium (ISP 8) | G | Moderate, yellowish white |
| | AM | Scant |
| | S | Abundant sporulation on the aerial and vegetative mycelium |
| | SP | Not produced |
| Bennet's agar medium | G | Good, yellow-brown - bright yellow-orange |
| | AM | Scant |
| | S | Abundant sporulation on aerial and vegetative mycelium |
| | SP | Not produced |
| Calcium malate agar medium | G | Good, yellowish-white |
| | AM | Scant |
| | S | Sporulation on the aerial mycelium |
| | SP | Not produced |
| Nutrient agar medium | G | Good, light yellow-brown |
| | AM | Not produced |
| | S | No sporulation |
| | SP | Not produced |

*In the above table, the symbols in the "Items" column have the following significance:
G: Growth; AM: Aerial mycelium; S: Sporulation; SP: Soluble pigment.

3. Physiological Properties

| | |
|---|---|
| Production of melanoid pigments (on peptone/yeast extract/iron agar medium: | Negative |
| Hydrolysis of starch: | Positive |
| Liquefaction of gelatin: | Positive |
| Coagulation of skim milk: | Negative |
| Peptonization of skim milk: | Positive |
| Assimilation of carbon sources: | |
| D-glucose | + |
| L-arabinose | +/− |
| D-xylose | + |
| Inositol | − |
| D-mannitol | − |
| D-fructose | +/− |
| L-rhamnose | + |
| Sucrose | +/− |
| Raffinose | − | where, +: positive assimilation; −: negative assimilation; +/−: doubtful.

4. Biochemical Properties

Amino acid composition of the cell wall:
contains L,L-diaminopimelic acid and glycine cell wall Type I)

| | |
|---|---|
| Major menaquinone: | MK9 ($H_6$), MK9 ($H_8$) |
| GC content of DNA: | 70.1% |
| Cellular fatty acids: | contains branched fatty acids |

5. Taxonomical Consideration

Determination of Genus

Streptomyces sp. MCI 2423 which produces inulo-oligosaccharides has the following characteristics:

1) It has perpendicular spore chains. Colonies are bright olive grey.

2) Formation of the aerial hyphae is scant. Most of the aerial hyphae develop into spores.

3) Vegetative hyphae in a culture medium are segmented to form spores.

4) In a liquid culture medium, fragmentation of the hyphae is observed.

5) Cell wall composition: contains L,L-diaminopimelic acid and glycine (cell wall Type I).

6) Major menaquinone: MK9 ($H_6$).

7) It contains branched fatty acids.

From these morphological and biochemical properties, this strain may be classified in the genus Streptomyces. Documented examples of Actinomycete wherein the vegetative hyphae are segmented are the genera Elytrosporangium, Microellobosporia, Chainia, Actinosporangium, and Actinopycnidium. Goodfellow et al (System. Appl. Microbiol. 8: 44–66, 1986), in view of the fact that these genera have biochemical properties in common with the genus Streptomyces, treat them as synonyms for the genus Streptomyces.

Determination of Species

This strain MCI 2423:

1) forms perpendicular spore chains, and 2) has bright olive grey colonies.

These facts suggested, from an examination of the ISP Microbial Species Table for the genus Streptomyces (Hideo Nonomura, Hakko Kogaku Zasshi, Vol.52, No.2, pp.78–92, 1974), that the strain belongs to the section Rectus-white.

Related microorganisms include *S. candidus, S. albovinaceus, S. setonii, S. sindenensis, S. albidoflavus*, and S. gougeroti. On comparing the properties of this strain (MCI 2423) with those of the species described in the ISP Classification, no reports for the fragmentation of the vegetative mycelium were found in the ISP species, and thus this strain is different from them.

Further, on comparing the morphological and physiological properties described in original reports of species in the genera Elytrosporangium, Micorellobosporia, Actinosporangium and Actinopycnidium with those of this strain (MCI 2423), this strain was clearly different from those species. We therefore identified this strain as Streptomyces sp. MCI 2423.

The morphological characteristics, and the physiological and biochemical properties, of Aureobacterium sp. MCI 2494 (hereinafter referred to as MCI 2494) are as follows:

1. Morphological Characteristics

Characteristics of colonies cultured on heart infusion agar medium at 30° C. for 1 week:

| 1) Shape: | Circular |
|---|---|
| 2) Size: | 2-4 mm |
| 3) Surface rising: | Convex |
| 4) Surface form: | Flat and smooth |
| 5) Lustre: | Dull |
| 6) Colour: | Grey changing to yellow |
| 7) Transparency: | Translucent |
| 8) Fringe: | Entire |

Characteristics of colonies cultured on heart infusion agar medium at 30° C. for 3 to 48 hr:

1) Cell Morphology

Cells extend irregularly into filamentous cells and branch up to about 7 to 24 hr after the cultivation. Subsequently septums are formed at various places in filamentous cells, segmentation gradually occurs in the septum areas, and then the cells change into a short rod- or rod-shaped cell structure.

| 2) Cell division pattern: | Segmented |
|---|---|
| 3) Motility: | None |
| 4) Sporulation: | None |
| 5) Gram staining: | Positive |
| 6) Acid fastness: | Negative |

2. Physiological Properties

| 1) Growth under anaerobic conditions: | Growth slight but possible |
|---|---|
| 2) Growth in air: | Positive |
| 3) Catalase: | Positive |
| 4) Oxidase: | Negative |
| 5) O-F Test: | F |
| 6) Hydrolysis of gelatin: | Negative |
| 7) Litmus milk: | No change, no peptonization |
| 8) Reduction of nitrates: | Positive |
| 9) Dentrification: | Negative |
| 10) Methyl red test: | Negative |
| 11) VP Test: | Negative |
| 12) Production of indole: | Negative |
| 13) Production of hydrogen sulfide: | Negative |
| 14) Hydrolysis of starch: | Positive |
| 15) Use of citric acid (on Christensen medium): | Positive |
| 16) Use of inorganic nitrogen sources: | Positive |
| 17) Urease: | Negative |
| 18) Hydrolysis of casein: | Negative |
| 19) Production of DNase: | Negative |
| 20) Growth in 5% NaCl: | Negative |
| 21) Production of pigments: | Yellow pigment insoluble in water. May be extracted from the microorganisms by chloroform/methanol, etc. |
| 22) Temperature range of growth: | 15-37° C. |
| 23) pH of growth: | pH 5-9 |

24) Acid formation form carbohydrates

| Carbon source | MCI 2494 | A. liquefacies | A. terregens |
|---|---|---|---|
| 1 L-Arabinose | +/− | − | − |
| 2 Xylose | +/− | − | − |
| 3 Rhamnose | − | − | − |
| 4 Glucose | + | + | +w |
| 5 Fructose | + | + | +w |
| 6 Mannose | + | + | +w |
| 7 Galactose | +w | + | +w |
| 8 Sorbose | − | − | − |
| 9 Sucrose | + | + | +w |
| 10 Lactose | +/− | +/− | +/− |
| 11 Maltose | + | + | + |
| 12 Trehalose | +/− | − | − |
| 13 Cellobiose | + | +/− | +w |
| 14 Raffinose | + | +/− | +/− |
| 15 Dextrin | + | + | +w |
| 16 Starch | + | + | +w |
| 17 Inulin | − | +/− | − |
| 18 Glycerol | +w | + | +w |
| 19 Erythritol | − | − | − |
| 20 Adonitol | − | − | − |
| 21 Mannitol | − | − | − |
| 22 Dulcitol | − | − | − |
| 23 Sorbitol | − | − | − |
| 24 Inositol | − | − | − |
| 25 Albumin | + | +/− | +w |
| 26 Esculin | − | − | − |
| 27 Salicin | + | +w | +w |
| 28 α-methyl glycoside | − | − | − |

*observed 1-3 weeks after cultivation.
*+: positive; +w: weakly possitive; +/−: doutful; −: negative.
*a terregens factor (a growth factor containing vitamins etc.) is not added.

25) Assimilation of organic acids

| Organic acid | MCI 2494 | A. liquefacies | A. terregens |
|---|---|---|---|
| 1 Acetic acid | + | + | − |
| 2 Pyruvic acid | + | + | +w |
| 3 L-lactic acid | + | + | − |
| 4 Malic acid | + | + | +w |
| 5 Succinic acid | + | +/− | + |
| 6 Fumaric acid | + | + | + |
| 7 α-ketoglutaric acid | +/− | + | +/− |
| 8 Citric acid | +/− | + | − |
| 9 Formic acid | − | + | − |
| 10 Propionic acid | + | + | +/− |
| 11 Butyric acid | − | + | − |
| 12 Oxalic acid | − | − | − |
| 13 Malonic acid | − | +/− | − |
| 14 Adipic acid | +/− | − | − |
| 15 Pimelic acid | +/− | − | − |
| 16 Glycolic acid | − | − | − |
| 17 Glyoxalic acid | +/− | − | − |
| 18 Gluconic acid | + | − | + |
| 19 Hippuric acid | + | +/− | + |
| 20 Uric acid | − | − | − |
| 21 Glutaric acid | − | − | − |

*observed 1-3 weeks after cultivation.
*+: possitive assimilation; +w: possitive assimilation (weak); +/−: doubtful; −: negative assimilation.
*a terregens factor (a growth factor containing vitamins etc.) is not added.

3. Scientific Taxonomical Properties

| 1) GC content of th DNA: | 69% |
|---|---|
| 2) Amino acid composition of cell wall: | Ornithine |
| | Glycine |
| | Homoserine |

|   | -continued |
|---|---|
|   | Glutamic acid (part of which is hydroxy-glutamic acid) |
|   | Alanine |
| 3) Structure of interpeptide bridge: | type B. D-Glu-Gly-D-Orn |
| 4) Sugar composition of cell wall: | Rhamnose |
|   | Galactose |
|   | Unidentified hexoses |
| 5) Glycolate test: | Glycolyl type |
| 6) major menaquinone: | MK-13 |

4. Taxonomical Considerations

Position on the Higher Taxa

This strain (MCI 2494) has the following characteristics:

1) There are definite stages of filaments-rods-short rods in the cell cycle,

2) The GC content of DNA has a high value of 69%,

3) The diamino-amino acids of the cell wall is ornithine, and

4) The major menaquinone is MK-13.

From these characteristics, it was established that this strain (MCI 2494) belongs to the ornithine-containing species of the irregular, nonsporing and gram-positive rods listed in Bergey's Manual of Systematic Bacteriology, Vol. 2.

Determination of Genus

Distinguishing features of ornithine-containing genera:

| Charact-eristic | Cellu-lomonas | Curto-bac-terium | Aureo-bac-terium | MCI 2494 |
|---|---|---|---|---|
| Peptidoglycane type | A | B | B | B |
| Glycolate test (type) | Acetyl | Acetyl | Glycolyl | Glycolyl |
| Major menaquinone | MK-9(H4) | MK-9 | MK11-13 | MK-13 |
| GC content (%) | 71–76 | 68–75 | 65–76 | 69 |

As shown in the above table, this strain (MCI 2429) is characterized in that:

1) the peptidoglycane is type B, 2) the acyl type of peptidoglycan is glycolyl, and 3) the major menaquinone is MK-13.

This strain corresponds well to the characteristics of the genus Aureobacterium in Bergey's Manual of Systematic Bacteriology, Vol. 2, page 1323. This strain was however different from the genus Aureobacterium in that it grows into a filamentous cell in the initial stage of culture and grows slightly under anaerobic conditions. According to Bergey's Manual of Systematic Bacteriology, Vol. 2, classification of coryneform bacteria at the genus level should be based on chemical composition factors such as the amino acid composition of the cell wall, sugar composition, structure of interpeptide bridge, the acyl type of peptideglycan, menaquinone composition, and GC content of DNA, and this view is widely accepted by many taxonomists. In view of this data, it seems appropriate to treat the differences of the morphological and physiological properties of this strain as characteristic of the species level, and we therefore identified the strain (MCI 2429) as belonging to the genus Aureobacterium. According to Bergey's Manual of Systematic Bacteriology, Vol. 2, 6 species of the genus Aurebacterium are known. Insofar as this strain contains the major menaquinone MK-13, it is similar to *A. flavescens* and *A. terregens*. However, from the sugar composition of the cell wall and insofar as this strain does not require the terregens factor (see above), it is clearly distinct from the latter 2 species. Further, in morphological properties, this strain has elongated filamentous cells and branched cells, and is therefore again different from these 2 species. We therefore postulate that this strain is a novel species of the genus Aureobacterium. We shall however await future taxonomical considerations to decide on a formal name for the species, and for the time being, we identified it as Aureobacterium sp.

The culture of the strain MCI 2423 or MCI 2494, which produces the novel exo-type hydrolase of this invention, may be performed in any culture medium which contains nutrients normally used by microorganisms. More specifically, fructans such as fructo-oligosaccharides, inulo-oligosaccharides, inulin, and the like containing $\beta$-2-1'fructoside bonds may be used as substrates. Other components necessary for microbial growth may also be added, for example soy bean powder, wheat germ, corn steep liquor, cottonseed oil, meat extract, peptone, yeast extract, ammonium sulfate, sodium nitrate or urea may be added as sources of nitrogen, and, if desired, inorganic salts which give sodium, potassium, calcium, magnesium, cobalt, chloride, sulfate and other ions and vitamins may further be added to the medium. It is effective if the amount of a fructan added to the medium is, in the case of inulin for example, within the range of 0.5-20%.

The culture temperature is 20° to 37° C., and an appropriate culture time is 24 to 96 hr.

After the culture is complete, the novel exo-type hydrolase of this invention can be purified from the supernatant of the culture liquid by a suitable combination of the known methods, and one example of which is given below.

The microorganisms are removed from the culture liquid by a suitable means such as filtration, centrifugation or the like to obtain a supernatant followed by a dialysis thereof against distilled water. Ammonium sulfate is added to the dialysate obtained up to 40% saturation, the hydrolase is adsorbed on Toyopearl HW65F (TOSO Co., Japan) buffered with phosphate buffer (0.02M, pH 7.0) containing 40% saturated ammonium sulfate, and thereafter the column chromatography is performed. This is followed by elution with a linear gradient of from 40 to 0% ammonium sulfate. The active fractions of inulinase are collected and dialyzed against 20 mM phosphate buffer(pH 7.0). When the thus-obtained crude enzyme solution is passed through a DEAE-Toyopearl column (TOSO Co.), inulase activity is found in the non-adsorbed fractions. This enzyme solution is further separated by a molecular sieve using Toyopearl HW55F (TOSO Co.), and is then adsorbed on QAE-Toyopearl (TOSO Co.) equilibrated with 10 mM Tris-HCl buffer (pH 8.7). Thereafter elution is performed with a linear gradient of from 0 to 0.5% saline solution, the active fractions collected, and dialysis performed so as to obtain the purified novel exo-type hydrolase of this invention.

The purified enzyme of this invention obtained as described in Example 1 or Example 2 below has the following properties:

(a) The enzyme hydrolyzes a fructan every 3–4 fructoses from the terminal fructose thereof to produce inulotriose and/or inulotetrose.

With respect to 1-ketose-type oligosaccharides, the enzyme can hydrolyze pentose and higher oligosaccharides to produce both sucrose and inulotriose from pentose and both inulotriose and inulotetrose from heptose and higher oligosaccharides, respectively.

The production ratio of inulotriose ($F_3$) to inulotetrose ($F_4$) is determined by a chain length of the inulin; that is, if it is long, $F_4 > F_3$, while if it is short, $F_3 > F_4$.

(b) The optimum pH of the enzyme is 6–7, and it is stable at pH 5.0–10.0.

(c) The optimum temperature thereof at pH 6–7 is about 50° C., and it has a satisfactory activity at 40°–60° C.

(d) The enzyme is stable under the conditions of heat-treating at pH 6–7 and a temperature of up to 50° C. for 30 min.

The enzyme was left at pH 6.5 at various temperatures for 30 min, then the reaction was carried out at 50° C. and the residual activity measured. Up to 50° C. there was practically no decline of the activity, but at higher temperatures the activity was suddenly lost.

(e) The molecular weights as determined by electrophoresis on a polyacrylamide gel are approximately 78,000 in the case of Example 1 and approximately 150,000 in the case of Example 2.

To manufacture inulotriose and/or inulotetrose using the enzyme of this invention, the enzyme is made to act on a fructan containing 4 or more fructoses, in particular on inulin, as a substrate. The enzyme which is actually used may be a purified enzyme obtained from a supernatant of the culture liquid or may be a supernatant obtained from the culture of the microorganism in a medium containing the above substrate. The enzyme or microorganism may be adsorbed, bound or entrapped on/in a support for immobilization by any of the known methods.

If the purified enzyme is used, for example, 0.01–10 units of the enzyme are added to 0.1M phosphate buffer (pH 6.5) containing 0.1 to 10% inulin, and the reaction is then carried out at 20°–50° C. for 5–100 hr to produce inulotriose and inulotetrose specifically from the initial stage of the reaction.

If the microorganism is cultured in a medium containing the aforementioned substrate, inulotriose and/or inulotetrose are produced in the culture liquid. The culture is freed of the microorganisms, and salts being an impurity are removed from the supernatant obtained by treating with active carbon and then demineralizing. Thus-obtained material is then subjected to an active carbon column chromatography. By the elution with a gradient of from 0 to 10% ethanol, inulotriose and/or inulotetrose are eluted at the concentration between 5 and 10%, and the inulotriose and/or inulotetrose in the supernatant are finally purified by removing ethanol.

The enzyme of this invention is a novel exo-type hydrolase which can specifically hydrolyze a fructan every 3–4 sugar units from the terminal fructose thereof. The enzyme can therefore be used effectively to manufacture inulotriose and/or inulotetrose.

This invention is illustrated in more detail by the following non-limited examples.

EXAMPLE 1

Streptomyces sp. MCI 2423 was inoculated in a liquid medium containing 1.5% inulin, 0.2% sodium nitrate, 0.05% magnesium sulfate, 0.05% potassium chloride, 0.05% pottasium dihydrogen phosphate, 0.02% yeast extract and a trace amount of iron chloride. After the strain was cultured in the above medium at 30° C. for 2 days, part of the culture was removed, transferred to the same medium (100 ml of the medium/500 ml conical flask), and cultured at 30° C. for 3 days under aeration and shaking.

After the culture was complete, the microorganisms were separated by centrifugation, and the supernatant obtained was then filtered through a membrane to give a crude enzyme solution.

Thereafter the crude enzyme solution was dialyzed against distilled water, and ammonium sulfate was added to the dialysate up to 40% saturation to precipitate the crude enzyme. The precipitate was then adsorbed on a Toyopearl HW65F column (I.D. 3 cm × L.30 cm) equilibrated with 20 mM phosphate buffer (pH 7.0) containing 40% saturated ammonium sulfate, and the enzyme was eluted with a gradient of from 40 to 0% saturated ammonium sulfate.

After dialysis of the active fraction against 20 mM phosphate buffer(pH 7.0), the dialysate was subjected to DEAE-Toyopearl column chromatography (column size: I.D.3 cm × L.15 cm), and the enzyme was further purified from the above non-adsorbed part by a molecular sieve using a Toyopearl HW55F column (I.D.2.1 cm × L.70 cm).

Then, the active fraction was also adsorbed on a QAE-Toyopearl column (I.D.2.1 cm × L.10 cm) equilibrated with 10 mM Tris-HCl buffer (pH 8.7), and eluted with a gradient of from 0 to 0.5M sodium chloride.

Table 1 shows the results of purification in each step. Using the above procedures, the novel exo-type hydrolase according to the invention was isolated and purified.

TABLE 1

| Step | Volume (m) | Total protein (mg) | Total activity (units) | Specific activity (units/mg) | Yield (%) | Purity (fold) |
|---|---|---|---|---|---|---|
| Crude enzyme fraction | 1450 | 131 | 31.9 | 0.24 | 100 | — |
| Toyopearl HW-65 | 86 | 7.23 | 15.3 | 2.11 | 48.0 | 8.6 |
| DEAE-Toyopearl | 90 | 4.03 | 15.3 | 3.80 | 48.0 | 15.6 |
| Toyopearl HW-55F | 32 | 1.63 | 7.20 | 4.42 | 22.6 | 18.1 |
| QAE-Toyopearl | 6 | 0.20 | 1.72 | 8.60 | 5.5 | 35.2 |

The activity of the enzyme was determined as follows.

0.15 ml of enzyme solution was added to a substrate mixed 0.25 ml of 0.2% aqueous inulin with 0.1 ml of 0.2M phosphate buffer(pH 6.5). The reaction was carried out at 37° C. for 1 hr, and the inulotriose and/or inulotetrose produced were determined by HPLC (high performance liquid chromatography). The amount of enzyme which can produce 1 umol of inulo-oligosaccharides per minute was regarded as 1 unit (u).

EXAMPLE 2

Aureobacterium sp. MCI 2494 was cultured by the same procedure as in Example 1. After culture, the culture was centrifuged, ammonium sulfate was added to the obtained supernatant up to 80% saturation to precipitate the crude enzyme, the precipitate was removed by filtration and suspended in a small amount of water, and dialysis was performed to obtain a crude enzyme solution.

The crude enzyme solution was adsorbed on a DEAE-Toyopearl 650M (TOSO Co.), and eluted with a gradient of from 0 to 0.3M saline. The active fractions of inulinase were collected, and separated by a molecular sieve using Toyopearl HW55 (TOSO Co.) so as to obtain an enzyme preparation showing a single band on electrophoresis. Table 2 shows the results of purification in each step.

TABLE 2

| Step | Volume (ml) | Total protein (mg) | Total activity (units) | Specific activity (units/mg) | Yield (%) | Purity (fold) |
| --- | --- | --- | --- | --- | --- | --- |
| Culture liquid | 800 | 2.95 | 616 | 5.20 | — | — |
| Salting-out | 10 | 1.64 | 201 | 3.06 | 32.6 | 0.59 |
| DEAE-Toyopearl | 2.4 | 0.076 | 38.1 | 12.5 | 3.2 | 2.41 |
| Toyopearl HW 55F | 0.8 | 0.0009 | 8.3 | 220 | 0.3 | 42.3 |

The activity of the enzyme was determined as in Example 1.

EXAMPLE 3

A solution containing 0.1 units of the purified hydrolase obtained in Example 1 was added to 1 ml of 0.05M phosphate buffer (pH 6.5) containing 0.1% (w/v) inulin as substrate, and the reaction was carried out at 30° C. for 10 min.

After heating the reaction solution to deactivate the enzyme, the amount of inulo-oligosaccharides produced in the solution was determined by HPLC. It was consequently found that inulotriose and inulotetrose were produced in proportion of 10.1% and 24.8%, respectively, other inulo-oligosaccharides being absent. Unreacted inulin accounted for 65.1%.

Inulotriose and inulotetrose can therefore be produced specifically by the novel exo-type hydrolase according to the invention.

EXAMPLE 4

A solution containing 0.1 units of the purified hydrolase obtained in Example 2 was added to 1 ml of 0.05M phosphate buffer (pH 6.5) containing 0.1% (w/v) inulin as substrate, and the reaction was carried out at 30° C. for 10 min.

After heating the reaction solution to deactivate the enzyme, the amount of inulo-oligosaccharides produced in the solution was determined by HPLC. It was cosequently found that 5.1 mg of inulotriose and 24.8 mg of inulotetrose were produced, other inulo-oligosaccharides being absent. Unreacted inulin accounted for 70.1 mg.

Inulotriose and inulotetrose can therefore be produced specifically by the enzyme of this invention.

EXAMPLE 5

The reaction was carried out as in Example 3 for 24 hr. Analysis carried out as in Example 3 showed that the total yield of inulotriose and inulotetrose was 81% (inulotriose:inulotetrose=4:6).

EXAMPLE 6

Streptomyces MCI 2423 was cultured according to the method of Example 1, 20 g of inulin was then added to 80 ml of the enzyme solution removed the microorganisms from the culture, and the reaction was carried out at 30° C. for 48 hr.

After the reaction, the reaction solution was analyzed by the liquid chromatography. The total yield of Inulotriose and inulotetrose was 73% (inulotriose:inulotetrose=4:6).

EXAMPLE 7

The reaction was carried out as in Example 3 for 2 hr. Analysis carried out as in Example 3 showed that the total yield of inulotriose and inulotetrose was 80% (inulotriose:inulotetrose=1:5).

EXAMPLE 8

The microorganism was cultured as in Example 2, 20 g of inulin was then added to 80 ml of the enzyme solution removed the microorganism from the culture, and the reaction was carried out at 30° C. for 48 hr.

After the reaction, the reaction solution was analyzed by the liquid chromatography. The total yield of Inulotriose and inulotetrose was about 75% (inulotriose:inulotetrose=1:5).

EXAMPLE 9

Five(5) l of culture was prepared according to the method of Example 2. After culture, the microorganisms were removed by centrifugation, and the supernatant was taken out as a crude enzyme solution. To 5 l of the crude enzyme solution, 80 ml (in the wet state) of highly porous and strongly basic ion exchange resin HPA75 (MITSUBISHI KASEI Co., Japan) buffered with 67 mM $KH_2PO_4$-$NaHPO_4$ buffer (pH 6.92) were added, thereafter the mixture was shaken at 30° C. for 3 hr to immobilize the enzyme on the resine. The suspension of the immobilized enzyme was washed 3 times with 100 ml of the above phosphate buffer (total volume 300 ml), and filtered with suction to obtain the wet, immobilized enzyme. This immobilized enzyme was packed into a column of internal diameter 20 mm and height 180 mm and maintained at 40° C. One hundred ml of water was passed through the packed column at a flow rate of 0.1 ml/min to stabilize the resin, then 1 l of 3% aqueous inulin was passed through the column at a flow rate of 0.1 ml/min to carry out the enzyme reaction therein. After the reaction, the eluent was decolored with active carbon, demineralized, and concentrated under reduced pressure. The same analysis as in Example 2 showed that 6.4 g of inulotriose and 16.9 g of inulotetrose have been produced.

We claim:

1. A method of manufacturing inulotriose and/or inulotetrose, comprising the steps of:
    reacting a fructan with an exo-type hydrolase capable of hydrolyzing a fructan only every 3 or 4 sugar units from a terminal fructose thereof, so as to produce inulotriose and/or inulotetrose; and recovering said inulotriose and/or inulotetrose.

2. A method according to claim 1, wherein said exotype hydrolase is produced by a microorganism which can produce said hydrolase.

3. A method according to claim 2, wherein the microorganism belongs to the genus Streptomyces.

4. A method according to claim 3, wherein the microorganism is Streptomyces sp. MCI 2423 (FERM BP-2678).

5. A method according to claim 2, wherein the microorganism belongs to the genus Aureobacterium.

6. A method according to claim 5, wherein the microorganism is Aureobacterium sp. MCI 2494 (FERM BP-2679).

* * * * *